United States Patent [19]

Bentley et al.

[11] Patent Number: 5,663,371
[45] Date of Patent: Sep. 2, 1997

[54] PROCESS FOR PREPARING POLYCYCLIC DYES

[75] Inventors: Stephen John Bentley, Lancashire; Ronald Wynford Kenyon; David John Milner, both of Manchester, all of United Kingdom

[73] Assignee: Zeneca Limited, London, England

[21] Appl. No.: 446,631

[22] PCT Filed: Nov. 8, 1993

[86] PCT No.: PCT/GB93/02296

§ 371 Date: May 25, 1995

§ 102(e) Date: May 25, 1995

[87] PCT Pub. No.: WO94/12577

PCT Pub. Date: Jun. 9, 1994

[30] Foreign Application Priority Data

Nov. 25, 1992 [GB] United Kingdom ............... 9224648

[51] Int. Cl.$^6$ .................................................. C07D 307/77
[52] U.S. Cl. ........................................................... 549/299
[58] Field of Search ............................................. 549/299

[56] References Cited

U.S. PATENT DOCUMENTS 5,214,161  5/1993  Milner ..................... 549/299

FOREIGN PATENT DOCUMENTS

| 75356 | 3/1983 | European Pat. Off. . |
| 75355 | 3/1983 | European Pat. Off. . |
| 252406 | 1/1988 | European Pat. Off. . |
| 518493 | 12/1992 | European Pat. Off. . |
| 2343785 | 10/1977 | France . |

OTHER PUBLICATIONS

Chemical Abstracts, vol. 91, No. 1, Jul. 1979, Pluman et al: "Alpha–dichlorobenzyl cyanide, a nieuw reagent for aromatic chlorination", p. 470, see abstract, & Pol.J.Chem. vol. 53, No. 1, @ 1979, pp. 201–203.

*Primary Examiner*—Joseph McKane
*Assistant Examiner*—Laura L. Stockton
*Attorney, Agent, or Firm*—Cushman Darby & Cushman IP Group Pillsbury Madison & Sutro LLP

[57] ABSTRACT

Described herein is a process for preparing a polycyclic dye which comprises reacting a compound of the Formula (2):

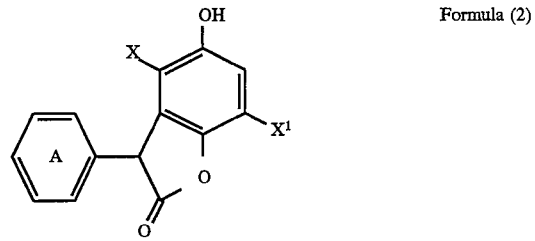

Formula (2)

with a compound of the formula:

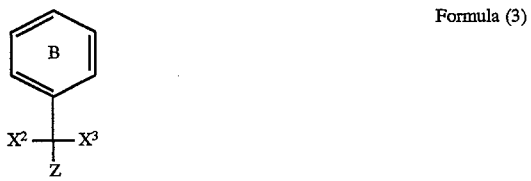

Formula (3)

wherein X and $X^1$ are, for example, hydrogen or halogen, $X^2$ and $X^3$ are halogen and Z is —CN, —$CO_2R$ or —$CONR^1R^2$ where R, $R^1$ and $R^2$ are, for example, alkyl. Processes for making compounds of Formulas (3) and (4) are also disclosed.

1 Claim, No Drawings

PROCESS FOR PREPARING POLYCYCLIC DYES

This application is a 371 of PCT/GB93/02296 filed Nov. 8, 1993.

The present invention relates to a process for the preparation of certain polycyclic dyes and to certain intermediates used the process.

According to the present invention there is provided a process for the preparation of a polycyclic dye of the Formula (1):

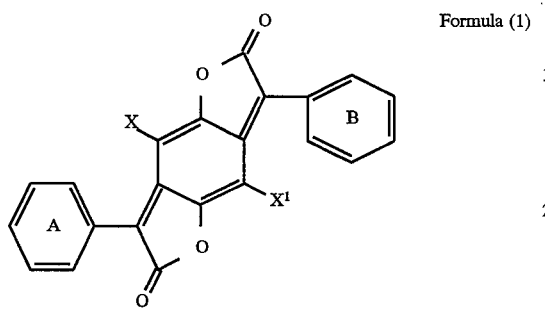

by reacting a compound of Formula (2):

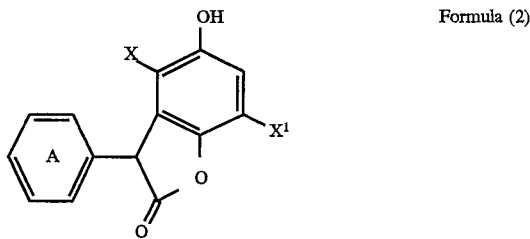

with a compound of Formula (3):

wherein:

Ring A is unsubstituted or is substituted by from 1 to 5 groups;

Ring B is unsubstituted or is substituted by from 1 to 5 groups;

X and $X^1$ each independently is —H, halogen, cyano, alkyl or aryl;

$X^2$ and $X^3$ each independently is halogen; and

Z is —CN, —$CO_2R$ or —$CONR^1R^2$ in which R is optionally substituted alkyl, optionally substituted aryl or optionally substituted aralkyl, and $R^1$ and $R^2$ each independently is —H, alkyl, aryl or aralkyl.

Where Ring A and Ring B are substituted by from 1 to 5 groups each group independently is selected from alkyl; alkoxy; alkoxyalkyl; alkoxyalkoxy; alkylcarbonyl; alkoxycarbonylalkyl; alkoxycarbonylalkoxy; alkylcarbonyloxyalkoxy; alkoxyalkoxycarbonylalkoxy; alkenyl; cyanoalkyl; cyanoalkoxy; hydroxyalkyl; hydroxyalkoxy; halogen, especially chlorine or bromine; hydroxy; cyano; nitro; alkylthio; arylthio; aryl; aryloxy; alkylsulphonyl; arylsulphonyl; —$NH_2$; —NHalkyl; —N(alkyl)$_2$; —NHCOalkyl and —NHSO$_2$alkyl; and preferably such groups in which each alkyl is $C_{1-4}$-alkyl, each alkoxy is $C_{1-4}$-alkoxy, the alkenyl is $C_{2-4}$-alkenyl and each aryl is phenyl.

Ring A is preferably unsubstituted or is substituted by groups selected from alkyl; alkoxy; alkoxyalkyl; alkoxyalkoxy; alkylcarbonyl; alkoxycarbonylalkyl; alkoxycarbonylalkoxy; alkylcarbonyloxyalkoxy; alkoxyalkoxycarbonylalkoxy; alkenyl; cyanoalkyl; cyanoalkoxy; hydroxyalkyl; hydroxyalkoxy; halogen, especially chlorine or bromine; hydroxy; cyano; nitro; aryl; aryloxy; alkylsulphonyl and arylsulphonyl; and preferably such groups in which each alkyl is $C_{1-4}$-alkyl, each alkoxy is $C_{1-4}$-alkoxy, the alkenyl is $C_{2-4}$-alkenyl and each aryl is phenyl. Ring A is more preferably unsubstituted or is substituted by groups selected from $C_{1-4}$-alkyl, $C_{1-4}$-alkoxy and $C_{2-4}$-alkenyl, and Ring A is especially unsubstituted or is substituted by $C_{1-4}$-alkoxy.

Ring B is preferably substituted by groups selected from —$NO_2$, $C_{1-4}$-alkoxy, $C_{1-4}$-alkyl, —$NH_2$, —NH(alkyl), —N(alkyl)$_2$, $C_{2-4}$-alkenyl and $C_{1-4}$-alkoxy-$C_{1-4}$-alkoxycarbonyl-$C_{1-4}$-alkoxy, Ring B is more preferably substituted by groups selected from —$NO_2$, $C_{1-4}$-alkyl, $C_{1-4}$-alkoxy, —$NH_2$, —NH(alkyl), —N(alkyl)$_2$ and $C_{1-4}$-alkoxy-$C_{1-4}$-alkoxycarbonyl-$C_{1-4}$-alkoxy and especially substituted by groups selected from —$NO_2$ and $C_{1-4}$-alkyl.

Ring A is preferably unsubstituted or is substituted by from 1 to 3 groups and more preferably is unsubstituted or is substituted by 1 or 2 groups and especially is unsubstituted or is substituted by 1 group.

Where Ring A is substituted by 1 group this group is preferably in the 4-position, where Ring A is substituted by 2 groups these are preferably in the 3- and 4-positions and where Ring A is substituted by 3 groups these are preferably in the 3-, 4- and 5-positions.

Ring B is preferably substituted by from 1 to 3 groups and more preferably by 1 or 2 groups.

Where Ring B is substituted by 1 group this is preferably in the 4-position and where Ring B is substituted by 1 or 2 groups these are preferably in the 3- and 4-positions.

It is especially preferred that Ring A is unsubstituted or is substituted in the 4-position by $C_{1-4}$-alkoxy. It is especially preferred that Ring B is substituted in the 4-position by —$NO_2$, $C_{1-4}$-alkoxy, $C_{2-4}$-alkenyl or $C_{1-4}$-alkoxy-$C_{1-4}$-alkoxycarbonyl-$C_{1-4}$-alkoxy; or that Ring B is substituted in the 4-position by —$NO_2$, $C_{1-4}$-alkoxy or $C_{1-4}$-alkoxy-$C_{1-4}$-alkoxycarbonyl-$C_{1-4}$-alkoxy and in the 3-position by $C_{1-4}$-alkyl.

Ring B is preferably 4-nitrophenyl and more preferably 3-alkyl-4-nitrophenyl and especially 3-methyl-4-nitrophenyl or 3-ethyl-4-nitrophenyl.

The halogen represented by X and $X^1$ is preferably —F, —Cl or —Br, more preferably —Cl or —Br. The alkyl group represented by X and $X^1$ is preferably $C_{1-6}$-alkyl, more preferably $C_{1-4}$-alkyl. The aryl group represented by X and $X^1$ is preferably phenyl.

X and $X^1$ are preferably —H.

The halogen represented by $X^2$ and $X^3$ is preferably —F, —Cl, —Br or —I, more preferably —Cl, —Br or —I and especially —Cl or —Br.

The alkyl group represented by R, $R^1$ and $R^2$ is preferably a $C_{1-6}$-alkyl and more preferably $C_{1-4}$-alkyl. The aryl group represented by R, $R^1$ and $R^2$ is preferably phenyl. The aralkyl group represented by R, $R^1$ and $R^2$ is preferably phenyl-$C_{1-4}$-alkyl, more preferably benzyl.

The alkyl group represented by X, $X^1$, R, $R^1$ and $R^2$ may be a straight or branched chain alkyl group each of which may be optionally substituted by one or more substituents selected from —$NO_2$, —CN, —OH, $C_{1-4}$-alkoxy-COO$C_{1-4}$-alkyl, —Cl, —F and —Br.

Z is preferably —CN, —$CO_2R$ or —$CONR^1R^2$ in which R, $R^1$ and $R^2$ each independently is $C_{1-6}$-alkyl, more preferably —CN, —CO$_2$C$_{1-6}$-alkyl or —CONH$_2$ and especially —CN, —CO$_2$CH$_3$, —CO$_2$C$_2$H$_5$ or —CONH$_2$.

Compounds of Formula (2) in which Ring B is substituted by a nitro group may be reduced by reaction with hydrogen in the presence of a palladium on carbon catalyst to the corresponding amino compounds.

The present process may be performed by heating the reactants in the presence of an acid condensing agent optionally in a liquid medium or by heating the reactants in an aprotic liquid medium in the presence of a base. The acid condensing agent is preferably an inorganic, more preferably a mineral acid such as sulphuric acid, or an organic acid, preferably a carboxylic acid such as formic, acetic or propionic acid or an alkyl- or aryl-sulphonic acid such as methanesulphonic, toluenesulphonic or dodecylbenzenesulphonic acid, or a Lewis acid such as zinc chloride or aluminium chloride.

The liquid medium is preferably an inert organic liquid, more preferably an aromatic hydrocarbon such as toluene or xylene, a halogenated aromatic hydrocarbon such as chlorobenzene or 1,2-dichlorobenzene, or a nitroaromatic such as nitrobenzene or nitrotoluene or is any of the inorganic or organic acids described above.

It is especially preferred that both the acid condensing agent and the liquid medium are carboxylic acids such as formic or acetic acids.

Where the reactants are heated in an aprotic liquid medium in the presence of a base the aprotic liquid medium is preferably a sulphone such as sulpholane, a sulphoxide such as dimethylsulptioxide or an amide such as dimethylformamide.

The process is preferably performed at a temperature from 50° C. to 200° C., more preferably at from 75° C. to 175° C. and especially at from 100° to 150° C. The reaction is preferably continued until substantially all the starting materials are consumed.

The product may be isolated by cooling the reaction mixture, diluting with water, filtering off and drying the precipitated solid.

The compound of Formula (2) may be prepared by reaction of dihydroxybenzene with an optionally substituted mandelic acid at an elevated temperature in the presence of an acid catalyst followed by pouring the reaction mixture into water and collecting the precipitated product by filtration.

According to a further feature of the present invention there is provided a process for the preparation of a compound of Formula (3) by reaction of a compound of Formula (4):

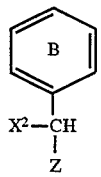

Formula (4)

wherein:

Ring B, X$^2$ and Z are as hereinbefore defined, with a halogenating agent.

The halogenating agent may be a halogen such as chlorine, bromine or iodine or may be a halogen carrier, preferably a hypohalite such as sodium hypochlorite.

The process is preferably performed in a liquid medium, more preferably in an organic liquid medium and especially in an alkanol such as methanol or ethanol.

It is preferred to perform the process in the presence of a base preferably an inorganic metal hydroxide such as sodium hydroxide or an inorganic alkoxide such as sodium methoxide.

The process is preferably performed at a temperature from –30° C. to 45° C., more preferably at from 15° C. to 35° C. and especially at from –5° C. to 25° C. Reaction is continued until substantially all the starting materials are consumed and the product is isolated by removing the liquid medium by distillation, dissolving the residue in a solvent such as dichloromethane, washing with water, separating and evaporating the organic phase to leave a residue which may be crystallised from a solvent such as ethanol.

The compound of Formula (4) may be prepared by reaction of a benzyl cyanide or substituted benzyl cyanide with SO$_2$Cl$_2$ to produce the corresponding 1-phenyl-1,1-dichloromethylnitrile followed, if desired by alcoholysis with an alkanol saturated with HCl to the corresponding ester. Alternatively where Ring B carries an electron-withdrawing substituent in the 4-position such as —NO$_2$ the compound of Formula (4) may be prepared by reaction of the corresponding nitrobenzene with a dihaloalcoholate in the presence of sodium methoxide.

According to a further feature of the present invention there is provided a compound of Formula (3) wherein Ring B, X$^2$, X$^3$ and Z are as hereinbefore defined, except for ethyl 2,2,-dichloro-2-(4-nitrophenyl)acetate.

The compounds of Formula (1) are useful as dyes particularly for the coloration of textile materials particularly synthetic textile materials such as polyesters.

The invention is further illustrated by the following examples:

EXAMPLE 1

Preparation of methyl 2-bromo-2-chloro-2-(3-methyl-4-nitrophenyl)acetate

A solution of bromine (4.3 g) in methanol (60 cm$^3$ parts) was prepared. A solution of sodium methoxide (5 cm$^3$ of 5.4 moldm$^{-3}$) was diluted with methanol (60 cm$^3$).

A mixture of methyl 2-chloro-2-(3-methyl-4-nitrophenyl) acetate (6 g) in methanol (20 cm$^3$) was stirred at room temperature and the solutions of bromine and sodium methoxide were added dropwise and simultaneously. The methanol was removed from the reaction mixture under vacuum and the residue was dissolved in dichloromethane. The dichloromethane solution was washed with water, separated and evaporated to have a residue which was recrystallised from ethanol to give yellow methyl 2-bromo-2-chloro-2-(3-methyl-4-nitrophenyl)acetate (4.0 g, 50%).

EXAMPLE 2

Preparation of 3-phenyl-7-(3-methyl-4-nitrophenyl)-2,6-dioxo-2,6-dihydrobenzo [1:2-b, 4:5-b']difuran:

A mixture of 5-hydroxy-2-oxo-3-phenyl-2,3-dihydrobenzofuran (0.1 part), methyl 2-bromo-2-chloro-2-(3-methyl-4-nitrophenyl)acetate (0.1 part) and acetic acid (10 parts) was stirred at ambient temperature for 15 minutes before heating to 50° C. The reaction mixture was stirred at 50° C. for 1½ hours before heating at 115° C. for 16 hours. The reaction mixture was cooled and poured into hydrochloric acid solution (100 parts of 10% w/w), stirred for 15 minutes and the precipitated solid was collected by filtration washed and dried 50° C. to give 3-phenyl-7-(3-methyl-4-nitrophenyl)-2,6-dioxo-2,6-dihydrobenzo [1:2-b, 4:5-b'] difuran (0.115 parts, 83.9%) λmax=463 nm in tetrahydrofuran.

EXAMPLE 3

Preparation of 3-(4-nitrophenyl)-7-(4-n-propoxyphenyl)-2,6-dioxo-2,6-dihydrobenzo [1:2-b, 4:5-b']difuran i) preparation of 1,1-dichloro-1-(4-nitrophenyl)-methylnitrile A mixture of 4-nitrobenzylcyanide (10.1 parts), chloroform (125 parts), water (162.5 parts) and sodium hypochlorite solution 87.5 parts of 15%) was stirred at 25° C.–38° C. for 10 minutes. The Chloroform layer was separated and washed with water and dried over anhydrous magnesium sulphate. The chloroform was removed under vacuum to leave 1,1-dichloro-1-(4-nitrophenyl)methylnitrile (11.55 parts) was a yellow oil.

ii)

A mixture of 5-hydroxy-2-oxo-3-(4-n-propoxyphenyl)-2,3-dihydrobenzofuran (0.7 parts), 1,1-dichloro-1-(4-nitrophenyl)methyl nitrile (1.0 part), precipitated calcium carbonate (1.0 part) and sulpholane (10 parts) was stirred and heated at 100° C.–110° C. for 1 hour before cooling and adding ethanol (45 parts) to precipitate a solid which was collected by filtration, washed with ethanol and dried. The solid was slurried in dilute hydrochloric acid, filtered, washed acid free, washed with ethanol and dried at 60° C. to give 3-(4-nitrophenyl)-7-(4-n-propoxyphenyl)-2,6-dioxo-2,6-dihydrobenzo ([1:2-b, 4:5-b']difuran (0.33 parts) λmax= 525 nm in chloroform.

EXAMPLE 4

Preparation of 3-phenyl-7-(4-nitrophenyl)-2,6-dioxo-2,6-dihydrobenzo [1:2-b, 4:5-b']difuran The procedure of Example 3ii) was followed except that 5-hydroxy-2-oxo-3-phenyl-2,3-dihydrobenzofuran was used in place of the 5-hydroxy-2-oxo-3-(4-n-propoxyphenyl)-2,3-dihydrobenzofuran to give 3-phenyl-7-(4-nitrophenyl)-2,6-dioxo-2,6-dihydrobenzo [1:2-b, 4:5-b']difuran.

EXAMPLE 5

Preparation of 3-phenyl-7-(4-nitrophenyl)-2,6-dioxo-2,6-dihydrobenzo [1:2-b, 4:5-b']difuran i) Preparation of methyl 2,2-dibromo-2-(4-nitrophenyl) acetate Nitrobenzene was treated with ethyl dibromoacetate in dimethylformamide containing potassium tertiarybutoxide at −20° C. to give ethyl 2-bromo-2-(4-nitrophenyl)acetate (1.37 parts) which was dissolved in methanol (50 parts). To this methanol solution was added dropwise separately a solution of bromine (1.72 parts) in methanol (40 parts) and a solution of sodium methoxide (0.56 parts) in methanol (40 parts). The reaction mixture was poured into dilute aqueous hydrochloric acid solution and extracted with dichloromethane. The dichloromethane solution was evaporated to give methyl 2,2-dibromo-2-(4-nitrophenyl)acetate (1.44 parts, 50%).

ii)

Methyl 2,2-dibromo-2-(4-nitrophenyl)acetate (0.15 parts) and 5-hydroxy-2-oxo-3-phenyl-2,3-dihydrobenzofuran (0.1 parts) were refluxed in acetic acid (20 parts) for 16 hours. The reaction mixture was poured into 10% aqueous hydrochloric acid and the precipitated solid filtered off, washed with water and dried to give 3-phenyl-7-(4-nitrophenyl)-2,6-dioxo-2,6-dihydrobenzo [1:2-b, 4:5-b']difuran (0.17 parts), λmax(CH$_2$Cl$_2$)=465 nm.

EXAMPLE 6

Preparation of 3-phenyl-7-(4-nitrophenyl)-2,6-dioxo-2,6-dihydrobenzo [1:2-b, 4:5-b']difuran i) Preparation of 2,2-dichloro-2-(4-nitrophenyl)acetamide A solution of methyl 2,2-dichloro-2-(4-nitrophenyl) acetate (1.36 parts) in dichloromethane (13.6 parts) was stirred with concentrated ammonia solution (10 parts) at 25° C. for 24 hours before diluting the reaction mixture with water (50 parts) and extracting with dichloromethane. The dichloromethane extracts were washed with water and evaporated to give 2,2-dichloro-2-(4-nitrophenyl)acetamide (0.86 parts, 63.4%) ($^1$Hnmr in D$_6$ dimethylsulphoxide 87.95 medium (2H), 88.23 broad (2H), δ8.35 medium (2H)).

ii)

2,2-dichloro-2-(4-nitrophenyl)acetamide (0.09 parts) and 5-hydroxy-2-oxo-3-phenyl-2,3-dihydrobenzofuran (0.1 part) were stirred in acetic acid (10 parts) at 115° C. for 108 hours. The reaction mixture was cooled and the precipitated solid was filtered off, washed with water and dried to give 3-phenyl-7-(4-nitrophenyl)-2,6-dioxo-2,6-dihydrobenzo [1:2-b, 4:5-b']difuran (0.019 parts, 13.6%), λmax(CH$_2$Cl$_{12}$) =466 nm.

EXAMPLE 7

Preparation of 3,7-diphenyl-2,6-dioxo-2,6-dihydrobenzo [1:2-b, 4:5-b']difuran ii)

Preparation of ethyl 2,2-dibromo-2-phenyl acetate

A mixture of ethylbenzoylformate (9.37 parts) and phosphorus pentabromide (24.9 parts) was stirred at 80° C. under nitrogen for 130 hours, a further two portions of phosphorus pentabromide (24.9 parts) were added. The reaction mixture was cooled to 25° C. and extracted with petroleum spirit (bp 60°–80° C.). The petroleum spirit extracts were washed with water, dried over anhydrous magnesium sulphate and evaporated. The product was purified by elution from silica gel using petroleum spirit/methylene chloride as eluant. Combination and evaporation of the eluate gave ethyl 2,2-dibromo-2-phenyl acetate (6.39 parts, 37%). Found C=37.2%, H=3.6% for C$_{10}$H$_{10}$Br$_2$O$_2$ requires C=37.29%, H=3.11%.

ii)

Ethyl 2,2-dibromo-2-phenylacetate (0.21 parts) and 5-hydroxy-2-oxo-3-phenyl-2,3-dihydrofuran (0.2 parts) were stirred in acetic acid (20 parts) at 115° C. for 41 hours. The mixture was cooled and the precipitated solid was filtered off, washed with water and dried to give 3,7-diphenyl-2,6-dioxo-2,6-dihydrobenzo [1:2-4:5 b']difuran (0.06 parts, 26.2%), λmax(CH$_2$Cl$_2$)=464 nm.

EXAMPLE 8

Preparation of 3-phenyl-7-(3-ethyl-4-nitrophenyl)-2,6-dioxo-2,6-dihydrobenzo [1:2-b, 4:5-b']difuran The procedure of Example 5 was used except that 2-ethylnitrobenzene was used in place of nitrobenzene.

3-phenyl-7-(3-ethyl-4-nitrophenyl)-2,6-dioxo-2,6-dihydrobenzo [1:2-b, 4:5-b']difuran was obtained as a brown solid λmax(CH$_2$Cl$_2$)=464nm.

We claim:

1. A process for the preparation of a polycyclic dye of the Formula (1):

Formula (1)

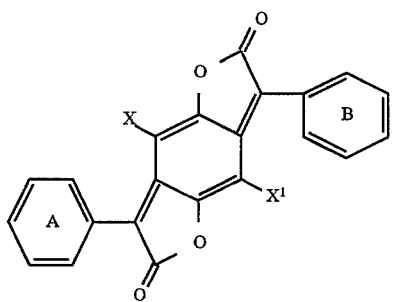

by reacting a compound of Formula (2):
with a compound of Formula (3):

Formula (3)

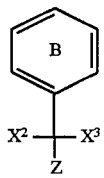

wherein:

Ring A is unsubstituted or is substituted by from 1 to 5 groups;

Ring B is unsubstituted or is substituted by from 1 to 5 groups;

X and $X^1$ each independently is —H, halogen, cyano, alkyl or aryl;

$X^2$ and $X^3$ each independently is halogen; and

Z is —CN, —$CO_2R$ or —$CONR^1R^2$, in which

R is optionally substituted alkyl, optionally substituted aryl or optionally substituted aralkyl, and $R^1$ and $R^2$ each independently is —H, alkyl, aryl or aralkyl, said process being performed at a temperature in the range of from 100° C. to 150° C.

* * * * *